(12) United States Patent
Vanjari et al.

(10) Patent No.: US 8,702,931 B2
(45) Date of Patent: Apr. 22, 2014

(54) LOW COST ELECTROCHEMICAL DISPOSABLE SENSOR FOR MEASURING GLYCATED HEMOGLOBIN

(75) Inventors: Siva Rama Krishna Vanjari, Bangalore (IN); Navakanta Bhat, Bangalore (IN); Sampath Srinivasan, Bangalore (IN); Bharadwaj Amrutur, Bangalore (IN); Chakrapani Kalapu, Bangalore (IN); Amit Kumar Mandal, Bangalore (IN)

(73) Assignee: Indian Institute of Science, Bangalore (IN)

( * ) Notice: Subject to any disclaimer, the term of this patent is extended or adjusted under 35 U.S.C. 154(b) by 0 days.

(21) Appl. No.: 13/449,333

(22) Filed: Apr. 18, 2012

(65) Prior Publication Data
US 2012/0261257 A1    Oct. 18, 2012

(30) Foreign Application Priority Data

Apr. 18, 2011    (IN) .......................... 1318/CHE/2011

(51) Int. Cl.
*G01N 27/327*    (2006.01)
*G01N 27/26*    (2006.01)

(52) U.S. Cl.
USPC ................ 204/403.06; 435/287.1; 422/68.1; 422/82.01; 205/792; 204/403.01

(58) Field of Classification Search
USPC ............ 204/403.01–403.15; 205/777.5, 778, 205/792; 422/68.1, 82.01; 435/287.1
See application file for complete search history.

(56) References Cited

U.S. PATENT DOCUMENTS

| | | | |
|---|---|---|---|
| 6,054,039 A * | 4/2000 | Shieh ............................. 205/778 |
| 7,943,385 B2 | 5/2011 | Yuan et al. |
| 8,394,325 B2 | 3/2013 | Campbell et al. |
| 2007/0173710 A1 | 7/2007 | Petisce et al. |
| 2010/0025264 A1* | 2/2010 | Yuan et al. .................. 205/777.5 |
| 2010/0089774 A1* | 4/2010 | Manohar et al. .............. 205/792 |

FOREIGN PATENT DOCUMENTS

EP    2356465 A1    8/2011
WO    WO/2010/043985 A1    4/2010

OTHER PUBLICATIONS

Zhong et al. (Adv. Funct. Mater. Mar. 2010, 20, 992-999).*
Bhat et al. (Apr. 7 & 8, 2011, IEEE/NIH Workshop).*
PowerPoint Presentation Chapter 11—Blood (Mosby 2008).*
Siva Rama Krishna V, Navakanta Bhat and Bharadwaj, Detection of Glycated Hemoglobin using 3-AminoPhenylboronic acid modified Graphene Oxide, 978-1-4577-0422-2/11 IEEE, Date 2011, pp. 1-4, Indian Institute of Science, Bangalore, India.

(Continued)

*Primary Examiner* — Jennifer Dieterle
(74) *Attorney, Agent, or Firm* — Narendra Reddy Thappeta

(57) ABSTRACT

Design of a disposable screen printed electrode (SPE) for sensing percentage glycated hemoglobin using electrochemistry is disclosed. SPE has four electrodes, one working electrode for the detection of glycated hemoglobin, one working electrode for the detection of hemoglobin and the other two electrodes are counter and reference electrodes that are common for both detection schemes. It also has a cellulose acetate membrane with lysis agents and surfactant embedded in it. Lysis agents lyse erythrocytes and release hemoglobin. Surfactants modify hemoglobin structure and enhance the rate the electron transfer and thereby the output signal during the electrochemical analysis. The SPE is low cost and user friendly. The only input from the user is a drop of blood.

12 Claims, 6 Drawing Sheets

(56) References Cited

OTHER PUBLICATIONS

Gabriele Halwachs-Baumann, Susanne Katzensteiner, Wolfgang Schnedl, Peter, Thomas Pieber, and Martie Wilders-Truschnig, "Comparative Evaluation of Three Assay Systems for Automated Determination of Hemoglobin" A1c, Clin. Chem., 43:3, pp. 511-517(1997).

Lionel Menard, M. E. Dempsey, L. A. Biankstein, H. Aleyasslne, M. Wacks, J. S. Soeidner, "Quantitativedeterminationof Glycosylated HemoglobinA1 by Agar Gel Electrophoresis", Clin. Chem 26/11, pp. 1598-1602(1980).

Jan-Olof Jeppsson, Uwe Kobold, John Barr, Andreas Finke, Wieland Hoelzel, Tadao Hoshino, Kor Miedema, Andrea Mosca, Pierluigi Mauri, Rita Paroni8, Linda Thienpont, Masao Umemoto, Cas Weykamp, "Approved IFCC Reference Method for the Measurement of HBA1C in Human Blood", Clin Chem Lab Med 2002; 40(1):pp. 78-89.

Frank Framtzen, Kjersti Grimsrud, Dag-Eric Heggli, Arne Ludvig Faren, Trond Løve\ly, Erlin Sundrehagen "Glycohemoglobin Filter Assay for Doctors' Offices Based on Boronic Acid Affinity Principle", Clin. Chem 43:12, pp. 2390-2396(1997).

Songqin Liu, Ulla Wollenberger, Martin Katterle, Frieder W. Scheller, "Ferroceneboronic Acid-Based Amperometric Biosensor for Glycated Hemoglobin", Sensors and Actuators B, 113, pp. 623-629, Feb. 27, 2006.

Seo Young Son, Hyun C. Yoon, "Electrochemical Analysis of Glycatedhemoglobin Based on the Biospecificity and Electron-Transferring Capability of Ferroceneboronic Acid", Biochip Journal, vol. 2, No. 2,pp. 116-122, 2008.

Jin-Young Park, Byoung-Yong Chang, Hakhyun Nam, Su-Moon Park, "Selective Electrochemical Sensing of Glycated Hemoglobin (HBA1C) on Thiophene-3-Boronic Acid Self-Assembled Monolayer Covered Gold Electrodes", Anal. Chem 2008, 80,pp. 8035-8044.

Ramesh, P. Bhagyalakshmi, V. Sampath, S., "Preparation, Physicochemical and Electrochemical Characterization of Exfoliated Graphite Oxide", J. Colloid Interface Sci.,2004,95, p. 274,pp. 1-8.

Xiaolei Zuo, Shijiang He, Di Li, Cheng Peng, Qing Huang, Shiping Song and Chunhai Fan, "Graphene Oxide Facilitated Electron Transfer of Metalloproteins at Electrode Surfaces", Langmuir, 2009, 26,3,pp. 1936-1939.

Peilin Yang, Qiang Zhao, Zhennan Gu, Qiankun Zhuang, "The Electrochemical Behavior of Hemgolobin on SWNTS/DDAB Film Modified Glassy Carbon Electrode", Electroanalysis, 2004,16, N0.-12, pp. 97-100.

Liying Jiang, Chunxiu Liu, Huaqing Li, Xianbo Luo, Yirong Wu and Xinxia Cai, "Performance of an Amperometric Biosensor for the Determination of Hemoglobin", J.Nanosci. Nanotech. 2005, vol. 5 , No. 8,pp. 1301-1304.

Shencheng Ge, Emily Woo, James G. White, and Christy L. Haynes, Electrochemical Measurement of Endogenous Serotonin Release from Human Blood Platelets, analytical chemistry, Mar. 8, 2011, pp. 2598-2604, ACS Publications.

CytoSep* Membrane, http://www.pall.in/main/oem-materials-and-devices/product.page?id=3897, downloaded circa Sep. 10, 2013, pp. 1-1.

The Major Components of Blood, http://www.nsbri.org/humanphys-space/focus3/earthphys-frame.html, downloaded circa Sep. 10, 2013, pp. 1-3.

Blood Seperation Membranes, http://www.ipocdx.com/pro_membranes.html, downloaded circa Sep. 10, 2013, pp. 1-1.

* cited by examiner

LOW COST ELECTROCHEMICAL DISPOSABLE SENSOR FOR MEASURING GLYCATED HEMOGLOBIN

RELATED APPLICATIONS

The present application is related to and claims priority from co-pending India provisional patent application entitled, "Disposable Screen Printed Electrode For Percentage Glycated Hemoglobin Sensor", application serial number: 1318/CHE/2011, filed on 18 Apr. 2011, naming as inventors Vanjari et al. and is incorporated in its entirety herewith.

TECHNICAL FIELD

Embodiments of the present disclosure relate generally to disposable sensors, and more specifically to a disposable sensor for measuring of percentage glycated hemoglobin.

BACKGROUND

As is well known in the relevant arts, glycated hemoglobin (GHb) is formed in a non-enzymatic glycation pathway by hemoglobin's exposure to plasma glucose, over 120-day lifespan of the red blood cell (RBC). A buildup of glycated hemoglobin within the red cell, therefore, reflects the average level of glucose to which the cell has been exposed during its life. It is always expressed as percentage of total hemoglobin.

Measurement of glycated hemoglobin levels may provide more accurate information on blood glucose levels over a long period of time (typically 120 days). In comparison, fasting blood glucose measurements merely indicate blood glucose levels over a much shorter period of time (typically on a daily basis). Estimation of percentage GHb may be valuable, for example, in devising optimum treatment strategies for long term management of diabetes. Various methods for the measurement of glycated hemoglobin are known in the art. Although techniques such as immunoassay, ion-exchange chromatography, electrophoresis, boronate affinity chromatography and high pressure liquid chromatography along with electrospray ionization mass spectrometry are commonly used in the laboratories, these techniques may be time consuming and may require bulky equipments. Other techniques to reduce the size of such equipments exploit the adsorption of GHb onto various materials like Zirconia nanoparticles, Aminophenyl boronic acid agarose beads, Thiophene-3-boronic acid on gold particles. However such materials may be associated with high costs, and designing these instruments may be complex. US patent no. 20100089774A1 discloses a screen printed electrode (SPE) system for detection of glycated hemoglobin and hemoglobin. However this method of detection involves elaborate use of buffers and reagents and uses potentiometric techniques to detect GHb. Addition of precise amount of liquid reagents, needs a lab technician with relevant experience and hence cannot be used by a common unskilled user. The present invention is directed towards the above problem and relates to easy to use disposable sensors for measuring percentage glycated hemoglobin in a blood sample. The inventors propose using a membrane modified with lysing agents, so that it can be used in miniaturized point of care devices for hemoglobin or glycated haemoglobin measurement. This technique eliminates the need for mixing in a separate lysis buffer which is a huge advantage in terms of making a point of care device both more user friendly and more robust. The inventors also propose the methodology for the specific detection of GHb and Hb.

SUMMARY

A disposable sensor for measuring glycated hemoglobin (GHb) and hemoglobin (Hb) has a GO-APBA (graphene oxide-3-Aminophenylboronic acid) coated working electrode and a GO modified working electrode. The sensor further has a reference electrode for maintaining potential and a counter electrode for maintaining charge balance and a salt-surfactant modified porous cellulose acetate membrane for lysing erythrocytes of blood cell samples and releasing hemoglobin molecules. The electrodes of the sensor are screen printed electrodes (SPE) and the lysis membrane is stitched on top of these electrodes. Detection of GHb is done using electrochemical impedance spectroscopy. A potential is applied between working electrode and reference electrode and the impedance between working electrode and counter electrode is determined. In another embodiment a two electrode system is used. The potential is applied between working and reference electrodes and the resultant current is measured between working and reference electrodes. A counter electrode is not used.

DETAILED DESCRIPTION

Various embodiments are described below with several examples for illustration. Example embodiments will be described with reference to the accompanying drawings briefly described below.

1. Sensor

Figures 1A, 1B:
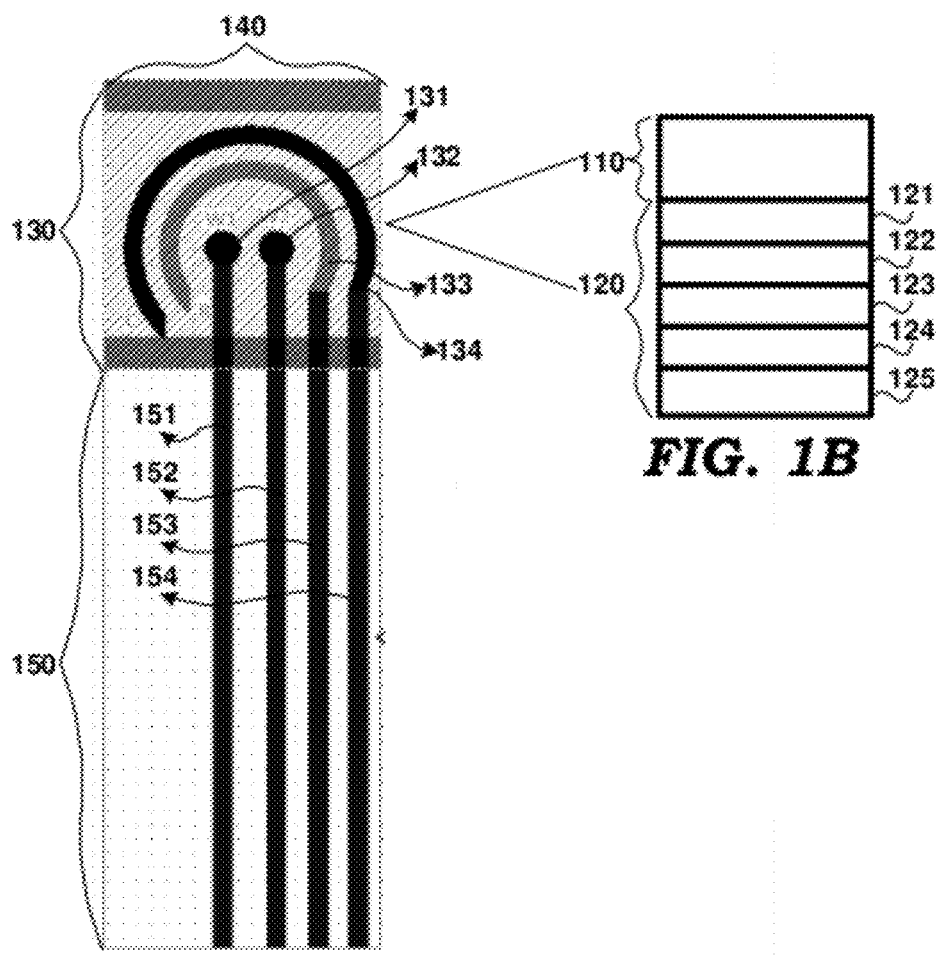
FIG. 1A depicts the design of a SPE strip to be used for the detection of GHb.
FIG. 1B shows the cross-sectional arrangement of the SPE strip. The layer 110 represents a membrane on to which a sample of blood is applied. The membrane is capable of lysing the erythrocytes in the blood and filtering the hemoglobin molecules through the pores. The filtrate comprising the hemoglobin molecules comes in contact with the SPE strip, 120 underneath, that can now detect and measure the hemoglobin and GHb present in the filtrate.

FIG. 1A and FIG. 1B show plan and elevation views respectively of a sensor 100 for the detection and measurement of hemoglobin (Hb) and GHb in a sample of blood, in an embodiment. Sensor 100 shown in elevation view in FIG. 1B is shown containing a membrane 110 and a screen printed electrode (SPE) 120. Membrane 110 is attached or stitched on the SPE 120.

Area formed by length 130 and width 140 in plan view of FIG. 1A represents the portion of sensor 100 containing membrane 110 and the portion of SPE 120 containing the electrodes for measurement of hemoglobin and glycated hemoglobin (GHb). This SPE system has four electrodes and is a combination of two individual three electrode systems, The electrodes shown numbered 131, 132, 133 and 134 respectively represent a first working electrode (W1) for measurement of Hb1Ac, a second working electrode (W2) for measurement of Hb, a reference electrode (R) and a counter electrode (C). Electrodes (R) and (C) are common for both the GHb and Hb measurements. Portion 150 contains electrical paths/tracks 151, 152, 153 and 154 connected respectively to 131, 132, 133 and 134, and facilitates connection of the electrodes to a device used for performing the GHb and Hb measurements. In an alternate embodiment the electrode 134 and the conductive track 154 can be eliminated. The SPE system then has three electrodes and is a combination of two individual two electrode systems.

Referring now to FIG. 1B, layer 125 is a substrate of sensor 100, and is made of poly-vinyl chloride (PVC). Any flexible substrate suitable for screen printing can be used as for example polymethyl methacrylate, epoxy-fiber composites, epoxy carbon composites, polyimide composites, phenolic strips and the like. Layer 121 of SPE 120 contains the electrodes 131, 132, 133 and 134 described above. Layer 121 is made up of either electroactive carbon and/or other electrode materials. Layer 122 is constructed using electro-active carbon. The contacts for the electrodes are made up of two layers viz., a conductive silver layer (124) and an electroinactive graphite layer (123) for protecting silver layer (124) from oxidation. In an alternate embodiment the silver track can be replaced by any highly conductive track such as copper, indium, brass, tin, alloys of metals like gold and so on. Layers 121-125 are typically printed using screen printing techniques.

Layer 110 (FIG. 2) represents a porous membrane comprising at least one embedded lysing agent used for lysing of cells in a sample of blood that is applied onto the membrane. A cross-sectional view and the mechanism of lysis of cells, when a drop of blood is applied onto porous membrane 110, are conceptually depicted in FIG. 2. Layer 210 represents a blood sample to be analyzed. Layer 220 represents porous membrane embedded with lysing agents. Layer 230 represents the filtrate (Hb and GHb components of erythrocytes) obtained by the porous action of the porous membrane 110.

The porous membrane of the invention may comprise embedded salts including, but not limited to ammonium chloride, potassium bicarbonate, saponin b and lithium salts. One skilled in the art will be able to optimize the lysis conditions for isolation of Hb and GHb from a sample of blood. The membrane may further comprise a hydrophilic surfactant like sodium dodecyl sulphate (SDS), cetyl trimethylammonium bromide (CTAB), octyl phenol ethoxylate (Triton X-100), polyethylene glycol tert-octylpheny ether (Triton X-114), the zwitterionic detergent (CHAPS), nonyl phenoxypolyethoxy ethanol (NP-40), polysorbate 20 (Tween 20). Didodecyldimethylammonium bromide (DDAB), Hexyltrimethylammonium bromide (HTAB), ethoxylated alcohols or phenols, betaines, Lauryl mono ethanol, sulphosuccinates, and so on. In some embodiments a double membrane system may be used. The membranes may be stitched together. One membrane may have lysis salts to isolate hemoglobin and detect GHb. The other membrane may contain salts and surfactant to enhance the electron transfer rate of hemoglobin.

The densely porous membrane layer may face electrode side while a porous layer may face air side. The pore size of the membrane can be decided based on the cell or protein that needs to be isolated. The diameter of hemoglobin is 5.5 nm and the size of human body cells ranges from 2 to 120 µm. In order to isolate other cells and allow only hemoglobin to pass through, it is therefore sufficient to have an average pore diameter of 1.5 µm or less. The dense skin layer has pores with an average diameter of 1.5 µm. The presence of macrovoids of diameters greater than 10 µm in the porous sub layer helps in allowing blood to pass through easily. Hence it is preferable to place the blood on top of the porous sub layer.

2. Working

In one embodiment of the invention, the working electrode 131 has been modified by the methods described below, for the adsorption of glycated hemoglobin. As the working electrodes 131 and 132 come in contact with the filtrate comprising Hb and GHb, the electrode 131 will adsorb GHb while the working electrode 132 detects the total Hb, facilitating the transfer of charge to and from the GHb or total Hb when a potential is applied between 131 or 132 and the reference electrode 133. The electrode 131 may be modified by appropriate compounds and processes, as described below, to enable the adsorption of GHb. Similarly, the electrode 132 may be designed for the detection of total hemoglobin. The electrode, 133 has a known potential to gauge the potential of the working electrode, while also balancing the charge added or removed by the working electrode. Its only role is to act as reference in measuring and controlling the potential of the working electrodes 131 or 132 and at no point does it pass any current. The electrode 133, may be made of electroactive carbon or conductive Ag/AgCl paste. The counter electrode, 134 passes all the current needed to balance the current observed at the working electrode 131 or 132. The working electrodes 131 and 132 may be of at least 1 mm diameter and the reference and counter electrodes, 133 and 134 may be rings with a width of at least 0.5 mm. The distance between the working electrode and reference electrode or the reference electrode and counter electrode may be at least 0.5 mm. The presence of Hb and GHb can be detected by amperometric techniques such as cyclic voltammetry, differential pulse voltammetry and chronoamperometry. Electrochemical impedance spectroscopy may also be used.

The sensor of the present invention employs a three electrode system wherein the role of maintaining constant potential and balancing the charge are achieved by two electrodes, the reference electrode 133 and the counter electrode 134. In an alternative embodiment a two electrode system wherein the same electrode maintains a constant potential while passing current to counter redox events at the working electrode can be used.

Although the embodiments of the present invention describe a three electrode system, the invention cannot be limited to this. Other systems which have more electrodes, but their design principles are generally the same as the three electrode system may also fall within the scope of the invention. The electrodes may be formed by the technique of screen printing, other printing methods known in the art to form electrodes may be used. The sensor of the present invention made by the process of screen printing may be referred to as "Screen Printed Electrode or SPE" interchangeably. Although the electrodes of the present invention have been formed by screen printing, the invention cannot be construed to be limiting to screen printing.

Figure 3:
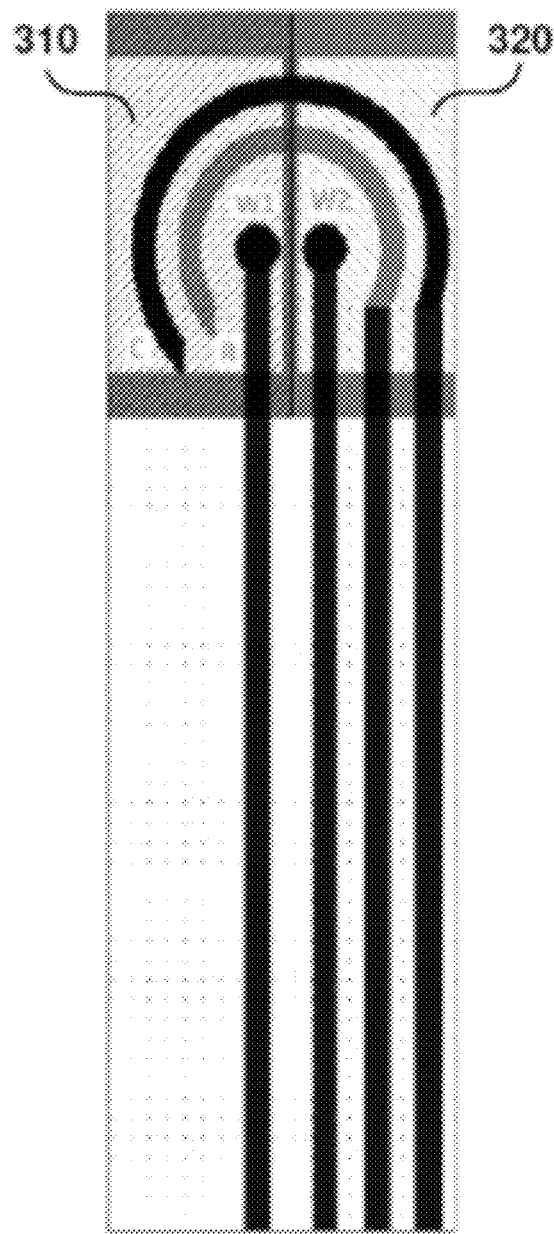
FIG. 3 depicts an alternative embodiment of the SPE strip.

In an alternative embodiment of the invention, two or more membranes with different parameters e.g., pore size, nature of embedded salts and surfactants, may be used together. One example provided here as depicted in FIG. 3 may comprise one membrane with lysing salts for isolation of hemoglobin and GHb. The other membrane may have lysing salts as well as the surfactant such as CTAB that is capable of denaturing hemoglobin. The detection of hemoglobin may be performed using the methods known in the art.

3. Synthesis of Composite for Specific Detection of GHb and its Use Thereof to Detect GHb.

Glassy carbon is widely used electrode in electroanalytical techniques. The term "Glassy Carbon" refers to non graphitizing carbon which combines glassy and ceramic properties with those of non graphitizing carbon allowing the electrode to have high resistance to temperature and chemical attack.

It is well known in the art that Graphene Oxide (GO) can act as an electrode material and has vast applications in developing biosensors. Graphene Oxide can be synthesized from exfoliated graphite by established methods known in the art. In the present invention the Hummers method has been used for the preparation of GO. Accordingly one working electrode of the current invention has been coated with GO.

Another aspect of the present invention is the reaction between GO with 3-aminophenyl boronic acid (APBA) to form a composite (GO-APBA) that can be coated on the working electrode. Since the ability of APBA to bind covalently to GHb is well documented in the art, the working electrode can be used in the SPE of the current invention for the detection of GHb. GO has carboxylic groups. In an embodiment, the carboxylic groups of GO are made to react with amine groups of 3-Aminophenylboronic acid to form the composite GO-APBA. Further, any boronic acid compound containing amine group can be made to react with GO and a new composite containing boronic acid can be formed by following the protocol described below.

Figure 4:
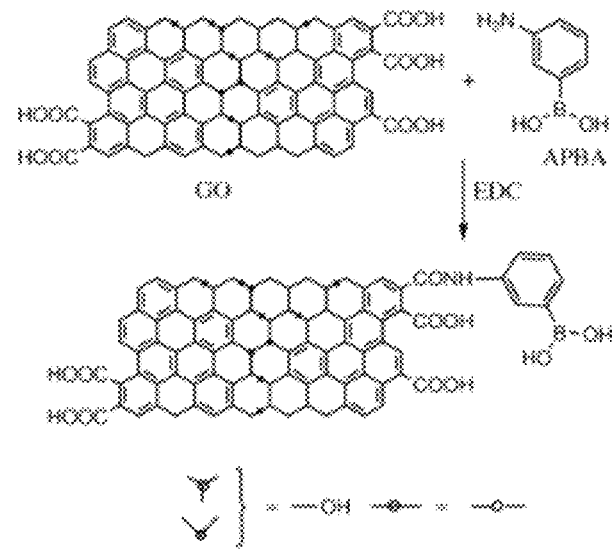
FIG. 4 is a schematic representation of the reaction between GO and APBA to form the product GO-APBA. The amide linkage formed in the presence of coupling reagent EDC is shown.

Synthesis of GO-APBA: An aspect of the invention is the chemical modification of GO with APBA. Accordingly GO at a concentration of 1 mg/ml and 10 mM of ethyl-3-(3-dimethylaminopropyl) carbodiimide (EDC) were added to deionized water and stirred continuously for 36 hrs. A 5 mM concentration of APBA was added to the mixture and stirred at room temperature for another 24 hrs. EDC being a coupling reagent aids in the formation of amide bond as shown in FIG. 4. The suspension was filtered and washed several times with water and ethanol, to remove any physically adsorbed APBA. The material was then dried in vacuum using silicagel.

Another aspect of the invention is the design of a modified electrode. The term "modified electrode" as used herein refers to an electrode whose surface has been coated with compounds or materials that are suitable for a particular application. In the present invention the GO-APBA prepared as described above was used to coat the working electrode such that the modified working electrode is capable of binding the GHb. The coating of electrodes can be done by any of the methods known in the art. In the invention described, a dispersion of GO-APBA prepared as described above, was drop cast on the GCE and allowed to dry for 2 hours and is used to detect GHb using Electrochemical Impedance spectroscopy. The same can be carried out with the working electrode of SPE (131) to detect GHb on SPE.

Modification of Cellulose acetate membranes: A further aspect of the invention is the preparation of modified cellulose acetate membranes for isolating total Hb. Thus, 10% (w/w) Cellulose acetate is dissolved in 80% (w/w) acetone and is mixed with 10% (w/w) water in which the lysing salts NH4Cl and KHCO3 are dissolved. A small amount of surfactant tween 80 is also added to ensure that the surface of the membrane is hydrophylic in nature. The mixture is sonicated to obtain a homogenous transparent solution. Membranes are cast using film casting knife on a nicely polished, cleaned BK-7 glass slides. Initial film casting thickness of 300 µm is enough to get porous membranes of 2 µm pore size which is sufficient to isolate hemoglobin. Within a few seconds after the casting, the slides were transferred into an inert atmosphere chamber and the solvents were allowed to evaporate in controlled environment.

The lysing salts get embedded into the membrane. It is known that surfactants enhance electron transfer rate of hemoglobin by denaturing it structure and releasing heme. Membranes can be modified with surfactants CTAB and the filtrate from these membranes contains denatured hemoglobin which can be analyzed electrochemically. Other salts and surfactants and their combinations may be used in the modification of the membranes.

Figure 2:
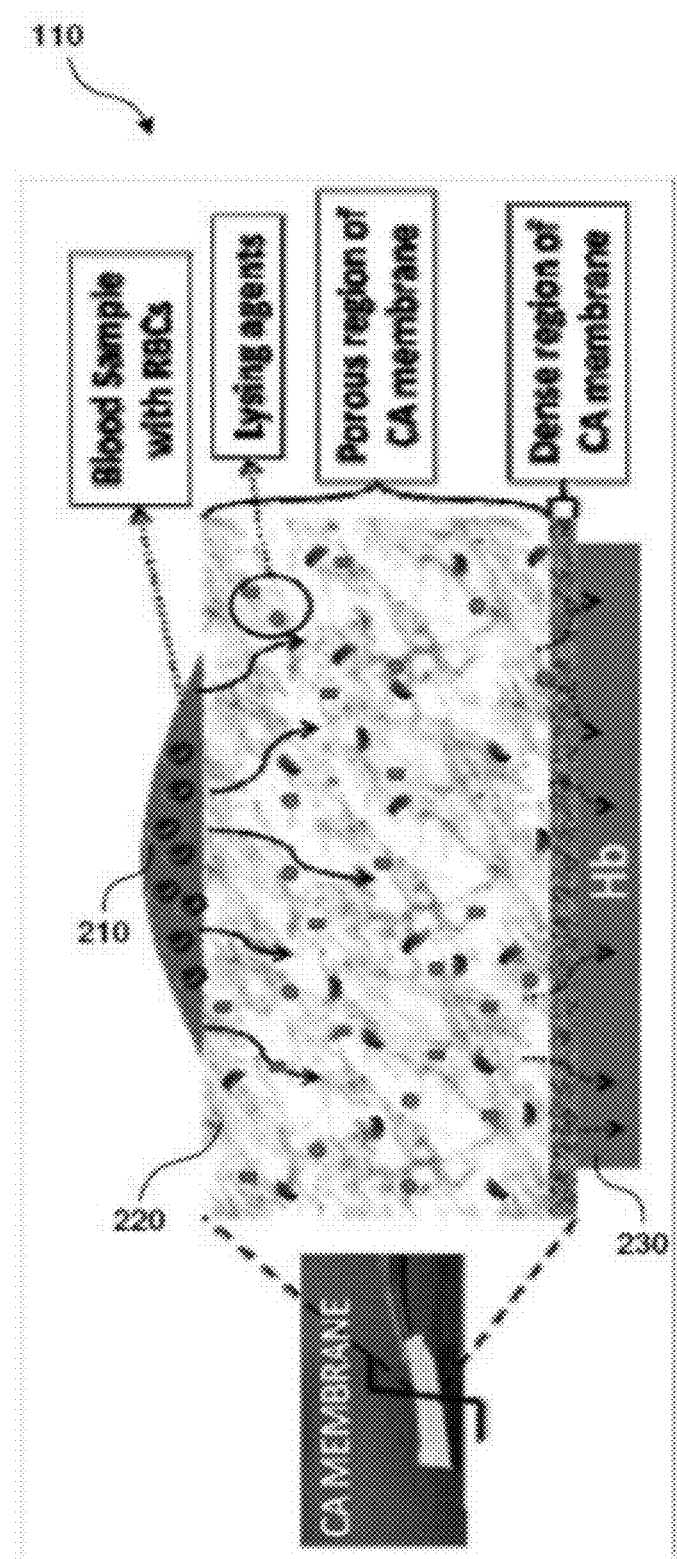
FIG. 2 shows a photograph of casted cellulose acetate membrane with a cross-sectional view of the membrane used for lysis and isolation of cellular components of a biological sample, in an embodiment of the present invention.

FIG. 2 shows a cross sectional view of the membrane. These salts act as lysing agents and the cellulose acetate membrane in which the salts are embedded acts as a filter. The salts are embedded inside the membrane during the membrane casting process, which is a controlled process as compared to the precipitation process. Unwanted cells get filtered out by the pores in the cellulose acetate membrane.

In another embodiment, these cellulose acetate membranes can be replaced with lysing agent modified nylon meshes. Though Hb is isolated in this case, the unwanted cells are not filtered out. Other polymeric meshes modified to suit the lysing requirements may also be used.

4. Detection of Glycated Hemoglobin

Figure 5:
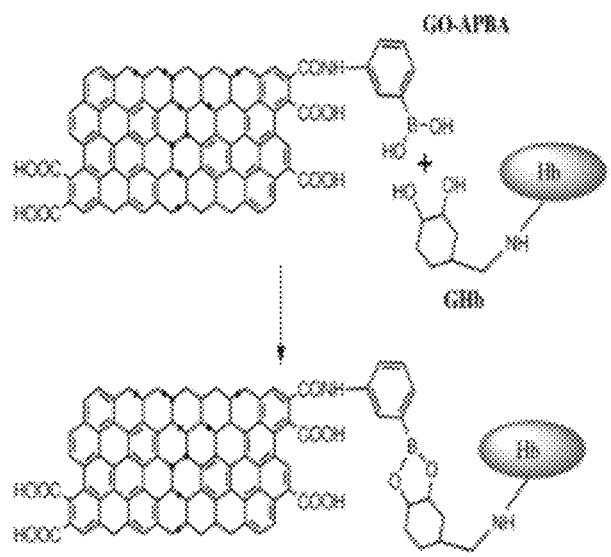
FIG. 5 represents the interaction between GO-APBA and GHb.

The GHb present in the filtrate has an affinity for APBA and gets immobilized on to the surface of the modified electrode, 131 through cis-diol bonds of glucose to boronic acid moiety. The chemical interaction of GHb with GO-APBA compound is shown in FIG. 5. A potential of 0.2V is applied between the working electrode and the counter electrode, and the impedance offered by the electrode for the electron transfer is measured between the working and counter electrodes.

Figure 6A:
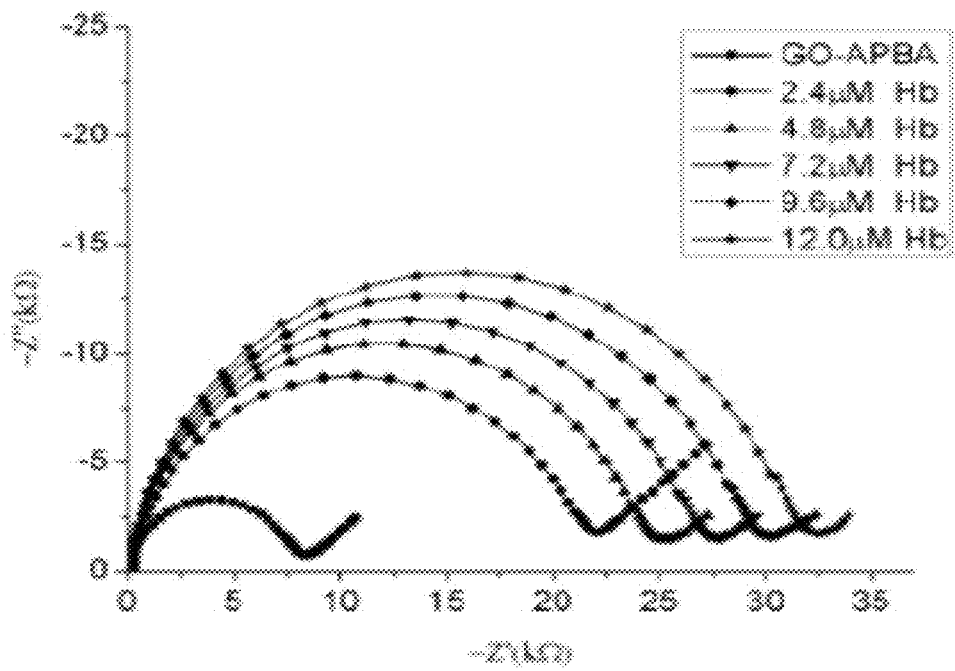
FIGS. 6A and 6B are respective Nyquist plots for GO-APBA modified electrode and for GO-modified electrode.
Figure 6B:
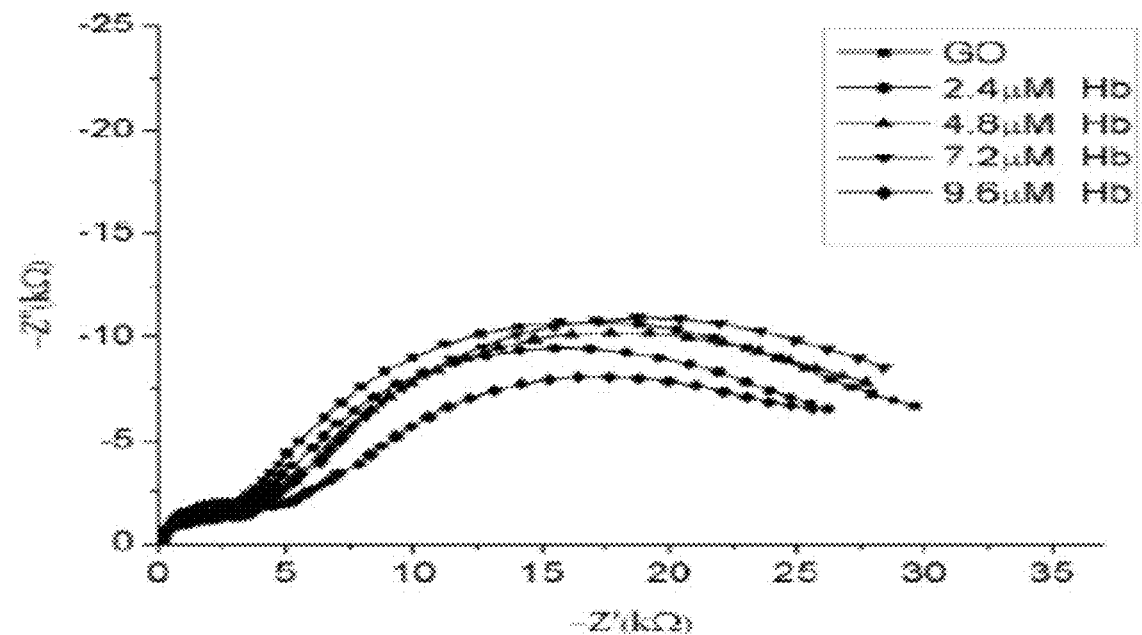
Figure 7:
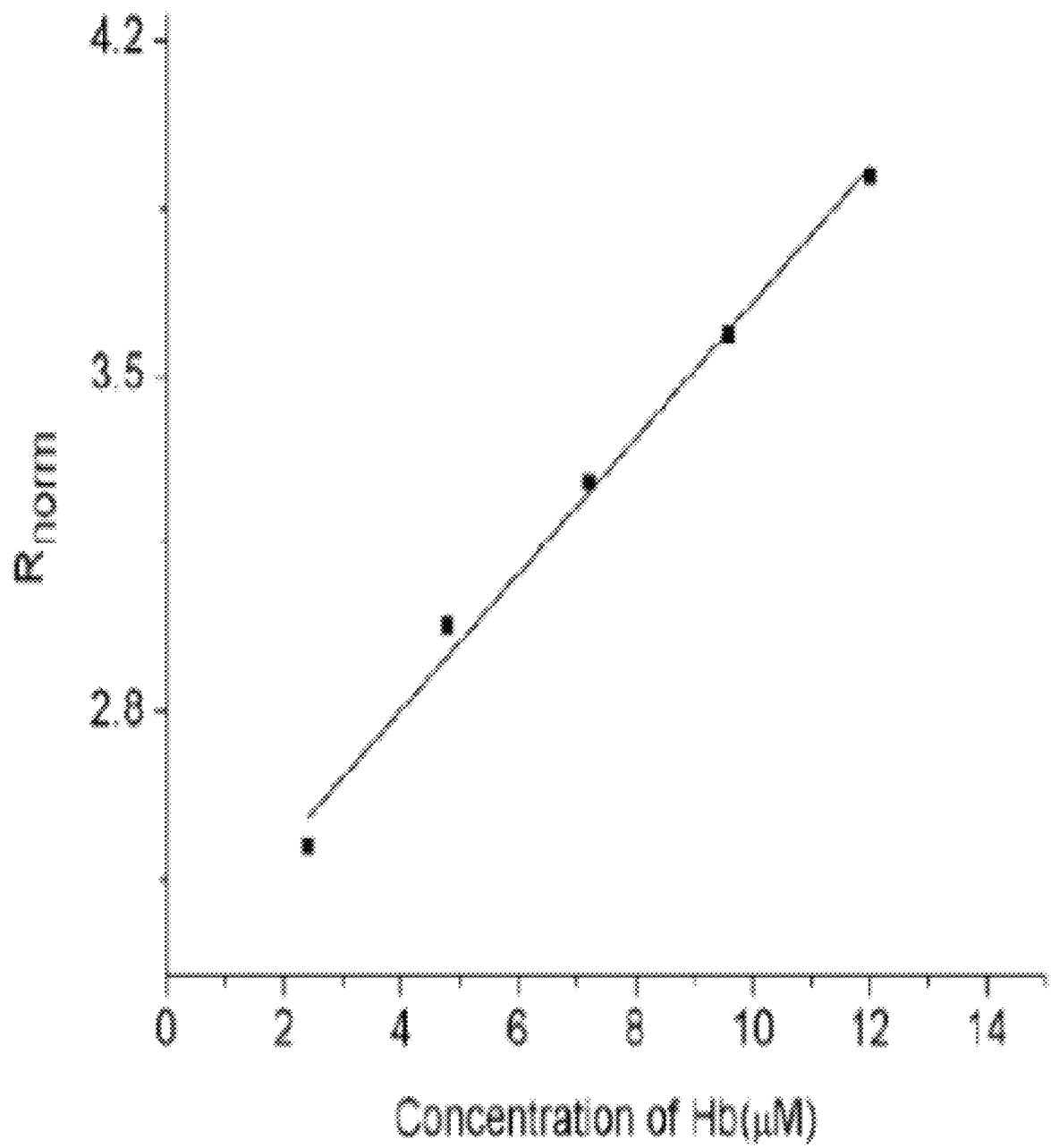
FIG. 7 is a plot of charge transfer resistance with respect to the concentration of Hb.

The chemical adsorption of GHb inhibits the electron transfer rate of the redox couple $[Fe(CN)_6]^{3-}/[Fe(CN)_6]^{4-}$ thereby increasing the charge transfer resistance ($R_a$). The diameter of the semicircle in the Nyquist plot in FIG. 6A, which is $R_{ct}$, increases with increase in the concentration of GHb. In order to eliminate the possible reason that physisorption may play a role in increase of $R_{ct}$, an experiment was performed using GO modified GCE. The corresponding Nyquist plots are shown in the FIG. 6B. The variation in $R_{ct}$ is small and is not systematic in this case. This proves that the increase in the charge transfer resistance is only due to the chemisorption of GHb onto the electrode surface. The increase in normalized charge transfer resistance is linear with respect to the concentration of GHb and is shown in FIG. 7.

Detection of Hemoglobin: It is well known in the art that hemoglobin consists of four protein chains with four heme portions ($Fe^{2+}$) buried deep inside the bulky hemoglobin molecule. The present invention exploits the redox potential and electron transfer ability of the heme portions. In one embodiment the method involves measuring the total hemoglobin in a sample by electrochemically measuring current due to $Fe^{2+}/Fe^{3+}$ redox reactions. The electrode potential is thus fixed at a level that allows for the heme molecule on the electrode surface to undergo electron transfer reaction. Therefore the current output observed will be proportional to the heme present which in turn is proportional to the concentration of hemoglobin in a test sample. To make the heme centers buried inside the molecule to be released before applying voltage, a current enhancing surfactant may be used. The surfactants used may be selected from Sodium Dodecyl Sulfate (SDS), Cetyltrimethylammonium Bromide (CTAB), DDAB, Tween 80 and TritonX-100 (TX-100). Standard amperometric techniques such as cyclic voltammetry, differential pulse voltammetry and chronoamperometry can be used to detect hemoglobin SPE action: SPE (FIG. 1) makes contact with the filtrate of the blood sample, obtained by the porous action of the membrane 110. The filtrate may contain the analyte, for example, Hb and GHb. As used herein an "analyte" may refer to any substance, chemical or biological constituent that is determined in an analytical procedure, for example the electroanalytical technique described below. In the present invention a drop of blood is applied onto layer 110 shown in FIG. 1B. Following the lysis of the blood and filtration action of the porous membrane, Hemoglobin molecules are collected under the membrane such that the filtrate comes in contact with the electrodes of the SPE layer 121 of FIG. 1B. GHb can be detected on the electrode 131 which is modified with GO-APBA compound as described above using electrochemical impedance spectroscopy or other amperometric techniques such as cyclic voltammetry, differential pulse voltammetry and chronoamperometry. For the detection of hemoglobin, electrode 132 is modified with Graphene oxide or surfactants like DDAB, SDS to detect Hb using standard amperometric techniques like cyclic voltammetry, differential pulse voltammetry and chronoamperometry. In another embodiment, the electrode 132 need not be modified, Instead the membrane can be embedded with surfactants like SDS, DDAB. Then filtrate is a denatured hemoglobin which can be detected directly on the electrode 132.

What is claimed is:

1. A sensor for measuring percentage glycated hemoglobin (GHb) and total hemoglobin (Hb), said sensor comprising:
    a salts-and-surfactant-embedded membrane to receive a blood sample, and for lysing erythrocytes in said blood cell sample to release hemoglobin molecules,
    said salts-and-surfactant-embedded membrane to allow said hemoglobin molecules and plasma to pass through as a filtrate, wherein said blood sample contains erythrocytes, white blood cells (WBCs), and platelets;
    a first working electrode to measure concentration of glycated hemoglobin (GHb) contained in said filtrate;
    a second working electrode to measure concentration of total hemoglobin (Hb) contained in said filtrate;
    a reference electrode to operate as a reference with respect to which measurements from said first working electrode and said second working electrodes are made; and
    a counter electrode for providing charge balance,
    wherein said salts-and-surfactant-embedded membrane has pores of small enough magnitude to retain any unlysed erythrocytes, said WBCs and said platelets, such that said filtrate passed through contains only said hemoglobin molecules and plasma.

2. The sensor of claim 1, wherein said electrodes are screen printed electrodes.

3. The sensor of claim 1, wherein said membrane is a porous asymmetric cellulose acetate membrane.

4. The sensor of claim 1, wherein said salts-and-surfactant-embedded membrane comprises a cellulose acetate membrane.

5. The sensor of claim 1, wherein said reference electrode and said counter electrodes have shapes selected from circles, squares, hexagons and pentagons around said working electrodes.

6. The sensor of claim 1, wherein said sensor is a bufferless sensor.

7. The sensor of claim 1, wherein said first working electrode is coated with GO-APBA (Graphene oxide-Aminophenyl Boronic Acid), said second working electrode is coated with GO (Graphene Oxide),
    wherein said GO is enabled to facilitate transfer of electron from heme of said Hb to said second working electrode, as a basis for said measurement of concentration of total Hb in said filtrate.

8. The sensor of claim 7, wherein said GO-APBA is obtained by the chemical modification of graphene oxide with amino phenyl boronic acid, wherein said chemical modification includes reacting GO (graphene oxide) with ethyl-3-(3-dimethylaminopropyl) carbodiimide (EDC) in the presence of deionised water.

9. The sensor of claim 1, wherein said porous membrane comprises a dense layer and an open porous sub layer, wherein the pores of said dense layer have an average diameter of less than or equal to 1.5 µm and greater than 5.5 nm to be able to retain cells remaining in said blood sample after said lysing.

10. The sensor of claim 9, wherein pores in the dense top layer allow hemoglobin and plasma to pass through.

11. The sensor of claim 9, wherein said membrane is attached on top of the electrodes such that the porous sub layer faces the air and the dense porous layer faces the electrodes.

12. The sensor of claim 9, wherein said salts-and-surfactant-embedded membrane is a porous polymeric membrane.

* * * * *